United States Patent [19]
Griss

[11] Patent Number: 5,536,268
[45] Date of Patent: Jul. 16, 1996

[54] SYSTEM FOR OSTEOSYNTHESIS AT THE VERTEBRAL COLUMN, CONNECTING ELEMENT FOR SUCH A SYSTEM AND TOOL FOR ITS PLACEMENT AND REMOVAL

[75] Inventor: Peter Griss, Marburg, Germany

[73] Assignee: Plus Endoprothetik AG, Switzerland

[21] Appl. No.: 284,645

[22] PCT Filed: Dec. 22, 1993

[86] PCT No.: PCT/EP93/03669

§ 371 Date: Aug. 16, 1994

§ 102(e) Date: Aug. 16, 1994

[87] PCT Pub. No.: WO94/14384

PCT Pub. Date: Jul. 7, 1994

[30] Foreign Application Priority Data

Dec. 23, 1992 [DE] Germany ............... 42 43 951.5

[51] Int. Cl.⁶ ................ A61B 17/70; A61B 12/86
[52] U.S. Cl. .................................. 606/61; 606/73
[58] Field of Search ................... 606/60, 61, 69, 606/70, 71, 72, 73

[56] References Cited

U.S. PATENT DOCUMENTS

5,176,680  1/1993  Vignaud et al. ............ 606/61
5,261,912  11/1993  Frigg ........................... 606/61
5,263,954  11/1993  Schlapfer et al. ............ 606/61
5,413,602  5/1995  Metz-Staunhagen ......... 606/60

Primary Examiner—Stephen C. Pellegrino
Assistant Examiner—Scott B. Markow
Attorney, Agent, or Firm—Andrus, Sceales, Starke & Sawall

[57] ABSTRACT

The present invention relates to a system for osteosynthesis at the vertebral column, in particular for stabilizing spinal segments including at least one rodlike connecting element (14) and at least two retaining units (12). Each retaining unit can be anchored to a spinal segment with a tuning-fork-shaped head, (15) the two limbs (16, 17) of which delimit an approximately U-shaped receptacle (18) for the connecting element (14) A clamping screw (19) can be screwed into the receptacle (18) to fix the connecting element (14) between the two limbs (16, 17) of the tuning-fork-shaped screw head (15) The floor (22) of the receptacle (18) has a concave shape to correspond to a swivel-bearing element (23) disposed between the floor (22) of the receptacle (18) and the connecting element (14) The element (24) has a bearing surface (24) faces the floor (22) of the receptacle (18) and, has a complementary convex curvature. The bearing surface (24) of the swivel-bearing element (23), facing the floor (22) of the receptacle (18), is dish-shaped, in particular hemispherical. The opposite side (25) of the element, which faces the clamping screw (19) in the assembled state, moreover includes a groove (26) to receive the rodlike connecting element (14).

19 Claims, 6 Drawing Sheets

SYSTEM FOR OSTEOSYNTHESIS AT THE VERTEBRAL COLUMN, CONNECTING ELEMENT FOR SUCH A SYSTEM AND TOOL FOR ITS PLACEMENT AND REMOVAL

BACKGROUND OF THE PRESENT INVENTION

The present invention relates to a system for osteosynthesis at the vertebral column, in particular for stabilization of spinal segments, to a connecting element for such a system, and to a tool for placement and removal of such a system.

In EP 0 441 729 A1 is disclosed such a system for osteosynthesis at the vertebral column, in particular for stabilization of spinal segments. This system comprises at least one rodlike connecting element and at least two retaining means, each of which can be anchored to a spinal segment, with a tuning-fork-like head, the two limbs of which delimit an approximately U-shaped receptacle for the connecting element. In addition this system comprises a threaded stopper, which can be screwed into the receptacle in order to fix the connecting element between the two limbs of the tuning-fork-like screw head. The floor of the receptacle is concave, and disposed between the floor of the receptacle and the connecting element is a round split ring the bearing surface of which, facing toward the floor of the receptacle, has a complementary convex shape. This system is intended to counteract the disadvantage of conventional systems, which ultimately derives from their special construction. That is, it is necessary for each of the retaining means to be very precisely placed at the corresponding spinal segment so that the connecting element can ultimately be mounted and permanently fixed to the at least two retaining means. In practice, however, the manipulation of this system according to EP 0 441 729 A1 has proved to require a relatively great effort during the surgical operation.

Other such systems for stiffening a part of the vertebral column comprising at least two vertebrae are known in the state of the art. These systems each comprise at least two screw-shaped or hook-shaped retaining means, each of which can be attached to one of the vertebrae of the affected part of the vertebral column. The retaining means are provided to receive and fix in position the connecting element that connects the retaining devices with one another. This arrangement is intended to achieve stiffening or so-called spondylodesis of individual parts of the vertebral column in cases of spinal curvature (scoliosis, kyphosis), injury (trauma), neoplasms (tumor) and in particular abrasion or degenerative spinal disease, according to the principle of osteosynthesis under conditions of the greatest possible rigidity, i.e. extreme mechanical stability.

The retaining means in these systems as a rule are screws, or so-called pedicle screws, or also special hooks, which in all cases are connected to one another by a mechanically stable connecting element in the form of a bending-resistant rod, a threaded rod or the like. To achieve a sufficiently great clamping action, the connecting element, which usually has an angular or shaped form, is received in conical cut-outs in the heads of the pedicle screws or hooks. However, these systems require the connecting element in its bearing to contact the pedicle screws or the hooks by way of a flat surface, so that an optimal clamping action is achieved on the basis of at least three-point contact. In practice it has turned out that in these systems the bearing surface is so small that the load is applied at only one point. Such punctate loading, during the everyday micromovements of the vertebral column, causes locally restricted, particularly high strain within the implant as a whole, which in turn causes loosening of the whole implant, wear with possible friction corrosion, deformation or even breakage. Another disadvantage of these systems is that they are relatively difficult to manipulate during the surgical operation, in order to achieve a precise fit and hence a strong clamping action. Often, therefore, it is hard to carry out a correction during the operation. The consequence, again, is a reduced constancy of the operation quality. Finally, the comparatively elaborate construction of these systems is disadvantageous, because on the one hand it limits their applicability for various indications and on the other hand it greatly increases the amount of space they take up, so that there is room for only a slight covering of muscle and skin.

SUMMARY OF THE INVENTION

The invention is therefore directed to the problem of providing a system for osteosynthesis at the vertebral column, in particular for the stabilization of spinal segments, which eliminates all the disadvantages known in the state of the art, in particular prevents high mechanical loading after implantation, which is considerably simpler to manipulate, not least because of a connecting element and/or tool specially designed for the system in accordance with the invention, and ensures constantly good operation quality.

As a result of the configuration in accordance with the invention, namely that the bearing surface of the swivel-bearing element—the surface facing the floor of the receptacle—is dish-shaped, in particular hemispherical, and that the opposite side—in the assembled state, the side toward the clamping screw—includes a groove to receive the rod-like connecting element, various advantages are produced simultaneously. One is that the dish-shaped, in particular hemispherical bearing surface produces a swivel-bearing element that allows an arbitrary orientation or adaptation to local conditions even during the surgical operation. This ensures that the rodlike connecting element can be received by the swivel-bearing element in such a way as to be precisely positioned. Another advantage is that the groove provided in the swivel-bearing element to receive the rodlike connecting element enables the connecting element to be seated in the associated retaining element over a large surface, with the consequence that the clamping action can be sufficiently strong without producing any punctate loading. As a result, the implant itself is more mechanically stable and has a longer operating life, because the connecting element is not subjected to additional danger of breakage, deformation or the like. Moreover, the manipulation or manipulability of this system during the surgical operation is considerably simplified. Thus in the actual operation only two components have to be manipulated, namely the rodlike connecting element on the one hand and the retaining means, with the swivel-bearing element and the clamping screw, on the other. This arrangement also allows additional correction at any time and with no difficulty during assembly, as well as self-correction and improvements in stabilization after the system is in place. An associated benefit is constant operation quality, reproducible at any time. Furthermore, the system in accordance with the invention, because of its decidedly simple construction, can also be employed for extremely diverse indications in which a part of the vertebral column comprising at least two spinal segments is to be stiffened. In addition, the structural design of the system in accordance with the invention is such that it occupies very little space, which ensures that it can be adequately covered with muscle and skin.

It is within the scope of the invention that the groove formed in the swivel-bearing element to receive the rodlike connecting element has an approximately semicircular cross section, corresponding to the cross section of the connecting element. Because of the largely matching cross sections of rodlike connecting element and groove in the swivel-bearing element, the rodlike connecting element has a large bearing surface, which achieves a strong clamping action without the production of punctate loading. Finally, because a straight or slightly bent rodlike connecting element can be arbitrarily longitudinally displaced within the groove of the swivel-bearing element, on account of the matching cross sections, after the clamping screw has been applied to the connecting element in the retaining means the connecting element can still be shifted in the axial direction as desired and simultaneously rotated about its long axis. As a consequence, it is possible to position the whole system precisely at the individual spinal segments in the corresponding part of the vertebral column, while at the same time the imposition of high stress on the connecting element in particular, which would greatly reduce the operating life of the implant, is avoided.

To further increase the clamping action, cross-ribs, in particular a fine-pitch thread, are machined into the surface of the groove.

Of particular interest with respect to permanent retention of the rodlike connecting element in the retaining means is the structure in which the inner end of the clamping screw, i.e. the end that acts on the floor of the receptacle or on the rodlike connecting element, is convex or conical, the conical tip in the latter case preferably being rounded. In this way the force is applied to the rodlike connecting element in a punctate manner, as a result of which a large-area contact between the clamping screw and the outer circumference of the rodlike connecting element is avoided. The clamping screw serves primarily to fix the rodlike connecting element within the receptacle of the retaining means, without determining the orientation of the rodlike connecting element with respect to the clamping screw. Hence it is readily possible to fix the rodlike connecting element within the receptacle of the retaining means while it is oriented in a direction not perpendicular to the long axis of the retaining means and/or the clamping screw.

Furthermore, characteristics are important in allowing the swivel-bearing element to swivel easily and hence allowing large-area contact between the rodlike connecting element and the swivel-bearing element. In one embodiment, the swivel-bearing element is held on the floor of the receptacle, in such a way that it can rotate both in a plane parallel to the plane passing through the receptacle and also in a plane perpendicular to that plane. In addition, because the swivel-bearing element is held on the floor of the receptacle of the retaining means, the system in accordance with the invention is decidedly compact and thus particularly simple to manipulate. With respect to its manipulation, the swivel-bearing element is part of the retaining means.

The above-mentioned swivelability with simultaneous permanent attachment of the swivel-bearing element to the receptacle of the retaining means may also be obtained. Here the swivel-bearing element is fixed to the floor of the receptacle by a pin projecting beyond the bearing surface of the swivel-bearing element, i.e. the surface facing the floor of the receptacle. The pin is held with slight pressing in a seating groove formed in the floor of the receptacle, the seating groove being oriented parallel to the plane passing through the receptacle.

A swivel-bearing element may be fixed to the floor of the receptacle by a pin projecting above the latter, which with slight pressing is held within a seating groove formed, preferably as a continuous groove, in the bearing surface of the swivel-bearing element, i.e. the surface facing the floor of the receptacle, the seating groove being oriented parallel to the seating groove for the rodlike connecting element.

As another and preferred alternative, the swivel-bearing element is fixed to the floor of the receptacle, by a retaining pin with proximally directed head, which with its distal end leading can be pressed through a slot in the swivel-bearing element that is oriented in parallel to the seating groove for the rodlike connecting element, into a corresponding receiving bore in the floor of the receptacle, until its head comes to rest within a head groove formed in the seating groove for the rodlike connecting element and oriented parallel to the above-mentioned slot.

In a further form of the invention, the head of the retaining pin, in the assembled state is recessed within the associated head groove. This arrangement ensures that when the swivel-bearing element is swiveled in a plane parallel to the plane of the slot in the swivel-bearing element, there is no possibility of collision between head and rodlike connecting element.

According to further features, the retaining pin is held by its distal end within the receiving bore in the floor of the receptacle, with a force fit or strong sliding fit. This arrangement ensures permanent as well as simple and hence inexpensive fixation of the retaining pin, and thus of the swivel-bearing element as a whole, to the floor of the receptacle of the retaining means.

By means of the alternative design in accordance with the invention, namely that the floor of the receptacle is made approximately in the form of a ball socket and that the swivel-bearing element consists of a spherical sleeve with radial gap or slit, which can be shifted along the connecting element, in addition to the advantages already mentioned the following other advantages are achieved. The swivelability of the rodlike connecting element with respect to the retaining means is still further improved as a result of the ball-socket-like shape of the floor of the receptacle on the one hand and by the construction of the swivel-bearing element as a spherical sleeve. The spherical sleeve together with the connecting element, after it has been secured with the clamping screw, can be swiveled with respect to the retaining means both in the median longitudinal plane of the retaining means over an angle $\alpha$ of 15° to 45°, preferably 30°, and also in the plane of the retaining means perpendicular to the median longitudinal plane of the retaining means over an angle $\beta$ of 1° to 20°, preferably 3°. Such an arrangement can be brought about, for example, by suitable choice of the distance between and/or the height of the two limbs of the approximately U-shaped receptacle for the connecting element. It is therefore possible to swivel the rodlike connecting element, after it has been secured but before it is fixed within the retaining means, easily in all planes, so that even bent connecting elements can be positioned as desired with respect to the adjacent retaining means.

In order to achieve a somewhat close fit even when the spherical sleeve together with the connecting element is first introduced into the receptacle of the retaining means, and the spherical sleeve can be seated largely without play in the receptacle of the retaining means.

Preferably the spherical floor of the receptacle, against which the spherical sleeve is brought to rest has a basically conical shape. In this way the spherical sleeve as well as the dish-shaped, in particular hemispherical swivel-bearing element according to the first alternative described above can be subjected to an additional clamping force by being pressed against the floor of the receptacle of the retaining means when the clamping screw is screwed further in. The adhesion between the spherical sleeve or swivel-bearing element and the floor of the receptacle of the retaining means can thus be increased many-fold.

With the second alternative, in order to increase still further the clamping action and also the size of the surface of the spherical sleeve that contacts the floor of the receptacle of the retaining means, the spherical sleeve is provided with a gap or slit oriented radially, approximately in the direction of the axis of rotation of the spherical sleeve, which endows the spherical sleeve with radial resilience. This radial resilience can be additionally increased by providing a groove, notch or the like at the inner wall of the sleeve, substantially diametrically opposite the above-mentioned gap or slit and oriented approximately in the direction of the axis of rotation of the spherical sleeve.

The spherical sleeve is preferably provided with several notches, channels etc. arranged on the outer surface and oriented approximately in the direction of the axis of rotation of the spherical sleeve, with which a tool such as a raspatory can be engaged to bring or move the spherical sleeve into an ideal clamping position, in which the gap or slit is positioned at the side, i.e. transverse to the long axis of the receptacle.

It is further within the scope of the invention to construct at least one retaining means as a pedicle screw with a screw thread, in particular a self-tapping thread, which simplifies implantation and at the same time enables the transmission of large forces.

In a preferred form of the invention the pedicle screw is slit longitudinally in the region of the first turns of the thread in order to remove shavings of the bone material of the spinal segment. In this way the hole in the bone within which the retaining means or pedicle screw is seated is created by removal of the bone material as the retaining means is screwed into the vertebra. The shavings of bone so produced become wedged into the subsequent turns of the thread, making it harder for the screw to turn and thus additionally preventing the retaining means from coming loose of its own accord.

The pedicle screw may be provided with a section between the receptacle and the screw thread that has the shape of a truncated cone tapering toward the screw thread, which fits closely into a corresponding previously routed-out excavation in the dense cortical bone material of the pedicle. Because this section contacts the very hard cortical substance over a large area, high shear forces imposed on the retaining means are well transferred.

Distance rings, distance sleeves etc. of varying axial width can be placed on the truncated-cone section, so as to enable the implantation of neighboring retaining means each at the same level. In this way the subsequent placement of the substantially rodlike connecting element is considerably facilitated.

In an alternative form of the retaining means at least one retaining means can also, equally advantageously, be constructed in the form of a hook to anchor the retaining means to the pedicle, below the articular process and at the transverse process. Here the shape of the hook itself corresponds to hooks that have previously been known and proven in use.

For the requirement that a part of the vertebral column is to be made particularly rigid, the connecting element is constructed as a bending-resistant rod.

To obtain punctate degrees of freedom of movement within the part of the vertebral column stiffened by a connecting element in the form of a rigid rod, at least one universal joint can be disposed between two retaining means. In a more detailed form of this embodiment, the universal joint is disposed between two parts of the connecting element. Here the universal joint comprises an approximately axially oriented and pot-shaped receiving element at one part of the connecting element and, disposed at the end of the other part of the connecting element, a flange-like thickening that can be received by the pot-shaped receiving element and has the form of a rounded disk, ball or the like. In particular, the thickening with the other part of the connecting element may be held within the pot-shaped receiving element of the one part of the connecting element by means of a threaded ring, spring ring or the like.

Furthermore, the universal joint may be advantageously constructed such that the two parts of the connecting element can move relative to one another in the axial direction, under elastic tension. Thus the universal joint permits not only a three-dimensional rotational movement but, in addition, a translational movement.

There is preferably disposed in the receiving element of the universal joint a (pressure) coil spring, inserted between the thickening and the threaded ring or the like attached to the receiving element.

As an alternative to constructing the connecting element as a bending-resistant rod, the connecting element can equally well take the form of a bendable wire, flexible cable or the like. In this way, depending on the longitudinal tension produced in the wire, cable or the like, an individually adjustable elastic, i.e. dynamic, connection between two retaining means can be obtained. Such a connecting element is particularly useful, for example, in the treatment of conditions of chronic pain in the lumbar region of the spine and also for the new formation of bone in the region of spondylodesis.

Furthermore, it is within the scope of the invention to construct the swivel-bearing element and/or the retaining means and/or the clamping screw and/or the connecting element of titanium, a highly stable titanium alloy or similar tissue-compatible material. In this way wear, corrosion and breakage can be minimized and, because of the low elastic modulus of these alloys, the mounting can be decidedly elastic, i.e. dynamic.

Likewise within the scope of the invention is a connecting element which is also suitable for conventional systems for osteosynthesis. Here the connecting element is constructed as a bendable wire, flexible cable or the like and consists of titanium, a titanium alloy or similar tissue-compatible material. Such a connecting element makes possible an individually adjustable and elastic, i.e. dynamic, connection between two retaining means on the basis of longitudinal tension produced in the wire, cable or the like, which can be varied to suit extremely specialized conditions. For example, flexibility of the wire or cable is favorable in the treatment of conditions of chronic pain in the lumbar region of the spine. Similarly, a connecting element in the form of a flexible wire, cable or the like is applicable in cases of new formation of bone in the region of spondylodesis. Quite apart from this, as a result of the bendable wire or cable the possibility of at least a slight relative movement between two adjacent spinal segments ensures that they become mutually aligned. In this way wear, corrosion and breakage can be avoided, and a decidedly high elasticity is achieved because of the low elasticity modulus of titanium or titanium alloys.

Further within the scope of the invention is a tool for installing and/or removing a system for osteosynthesis at the vertebral column, preferably for stabilizing spinal segments, which is also independent of the preceding claims. The tool in accordance with the invention comprises a routing instrument to excavate a recess in the bone material of the spinal segment, a first screw instrument to insert the retaining means into the bone material of the spinal segment and a second screw instrument to tighten the clamping screw after the swivel-bearing element with the connecting element has been mounted in the retaining means. With such a tool it is possible very rapidly, simply and reliably to install and/or remove a retaining means in the form of a pedicle screw.

In an advantageous form of the invention the routing instrument comprises a router with two axially sequential cutting surfaces to produce an excavation deeper inside the bone that has the shape of a truncated cone tapering into the bone material of the spinal segment, and an outer cylindrical excavation, such that the two excavations match the shape of a corresponding part of the retaining means that is placed in the bone material of the vertebra.

The routing instrument further may include a centering spike disposed in advance of the router, which is likewise equipped with a cutting surface for drilling.

The first screw instrument is preferably constructed such that the retaining means is attached at one end rigidly and detachably, with the median long axis of the retaining means coinciding with the shaft of the first screw instrument. In this way the retaining means can be exactly positioned in the previously cut excavation in the bone during the surgical operation. This arrangement also allows slight corrections of direction to be carried out in a simple manner.

An especially advantageous means of achieving such a construction is that the first screw instrument, includes a cross bar that can be fitted into the U-shaped receptacle of the retaining means, in particular a pedicle screw, so that the latter can be screwed in.

For the secure attachment of the retaining means to the first screw instrument, the first screw instrument may be provided with a threaded sleeve that can be displaced along the shaft, the threaded sleeve comprising an external thread that cooperates with the internal thread in the receptacle of the retaining means. The threaded sleeve preferably also includes at its outer circumference a knurled section, so that it can be more securely grasped.

To prevent the clamping screw from being lost during installation in the retaining means, a spring-loaded catch element may be provided.

BRIEF DESCRIPTION OF THE DRAWINGS

Additional characteristics, advantages and details of the invention will become apparent in the following description of some preferred embodiments of the invention, with reference to the drawings, wherein.

DESCRIPTION OF THE ILLUSTRATED EMBODIMENTS

Figure 1:
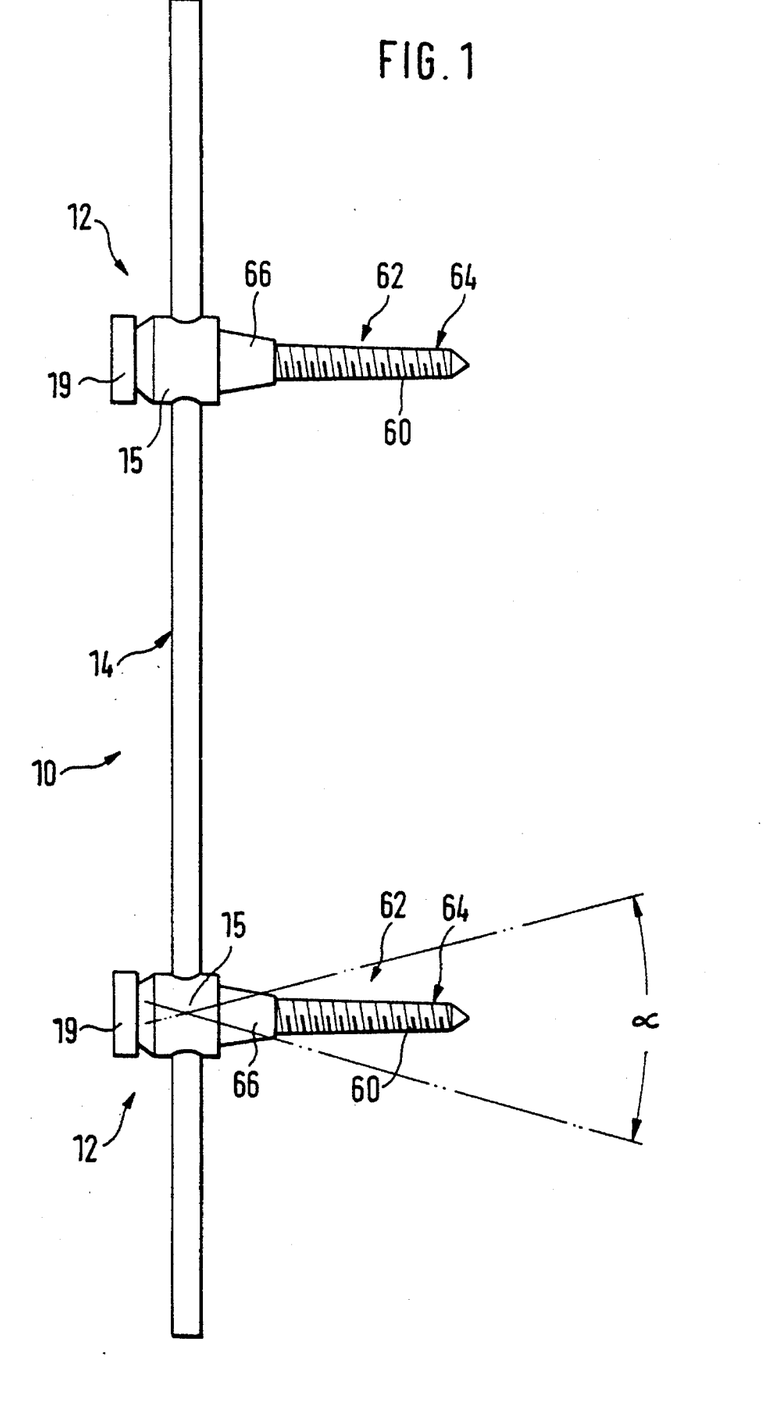
FIG. 1 is a side view of an embodiment of a system in accordance with the invention.

FIG. 1 shows an embodiment of a system 10 for osteosynthesis at the vertebral column, in particular for stabilizing at least two spinal segments (not shown). The system 10 comprises two retaining means 12, each of which can be anchored to a segment of the vertebral column.

The retaining means 12 is here constructed as a pedicle screw. This is screwed into the pedicle in a known manner, i.e. into the vertebral arch between spinous process, transverse process and the corresponding superior articular process. In an alternative form, however, the retaining means 12 can equally well be constructed in a hook shape (not shown). In this case the retaining means 12 is anchored or hooked in at the pedicle, under the articular process and transverse process, in a manner known per se.

The two retaining means 12 corresponding to FIG. 1 are provided to receive and fix in position one of the rodlike connecting elements 14 that connect the two retaining means 12 to one another. Depending on requirements, i.e. to suit the individual indication, the connecting element 14 consists either of a bending-resistant or largely bending-resistant rod or of a bendable wire, flexible cable or similarly elastic element. Suitable materials for such a rodlike connecting element 14 are titanium, a titanium alloy or a similar tissue-compatible material.

Figure 2:
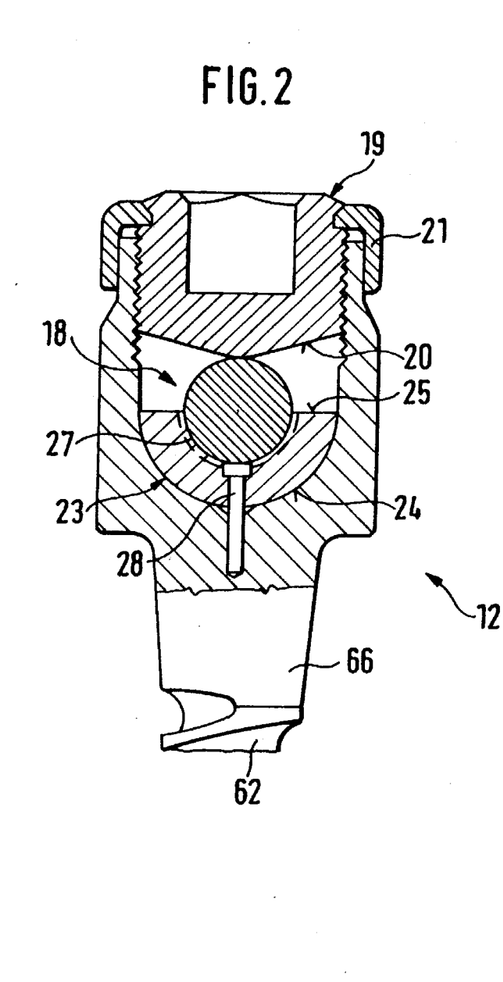
FIG. 2 is a partial median longitudinal section through an embodiment of a retaining means constructed in accordance with the invention with swivel-bearing element and connecting element in the assembled state, enlarged.
Figure 8:
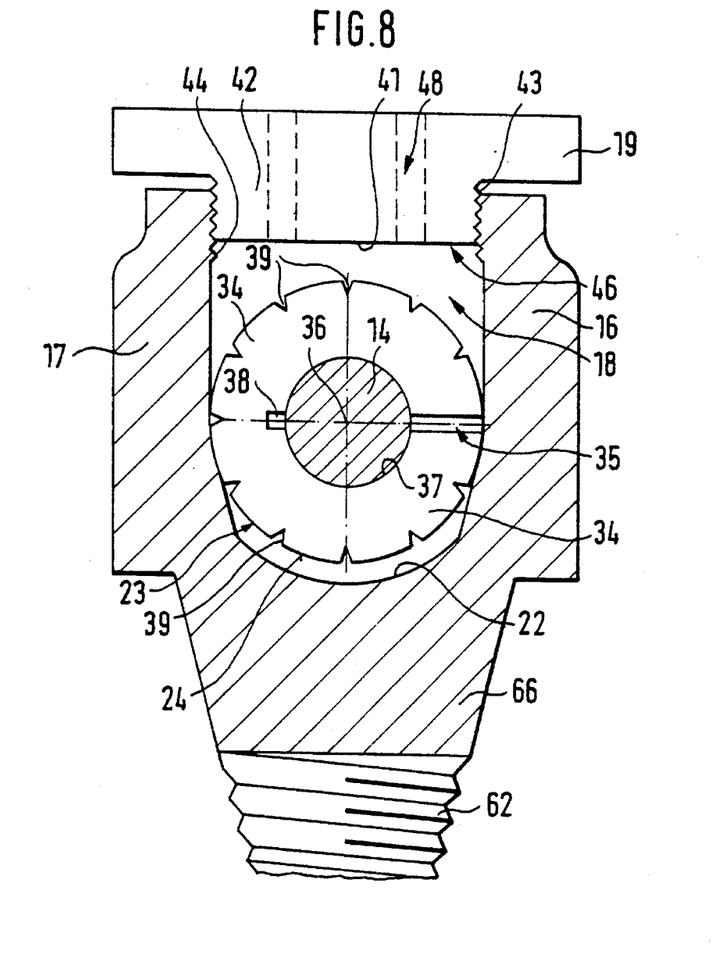
FIG. 8 is a partial median longitudinal section through an alternative embodiment of a retaining means constructed in accordance with the invention, with swivel-bearing element and connecting element in the assembled state, enlarged.

As shown in FIGS. 2 and 8, the retaining means 12 is provided with a tuning-fork-like head 15, the two limbs 16, 17 of which delimit an approximately U-shaped receptacle 18 for the connecting element 14. A clamping screw 19 to fix the connecting element 14 between the two limbs 16, 17 of the tuning-fork-like screw head 15 can be attached to the retaining means 12 by way of a threaded connection, i.e. can be screwed into the receptacle 18.

Figure 3:
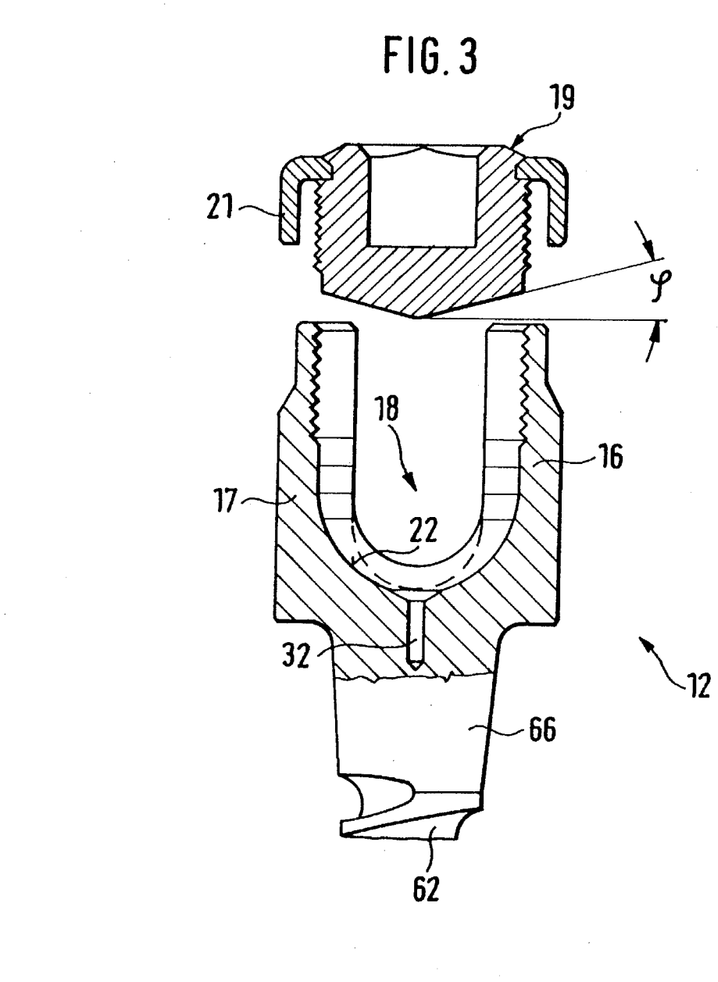
FIG. 3 is a partial median longitudinal section through the embodiment of the retaining means according to FIG. 2 without swivel-bearing element and connecting element, in the unassembled state, enlarged.
Figure 4:
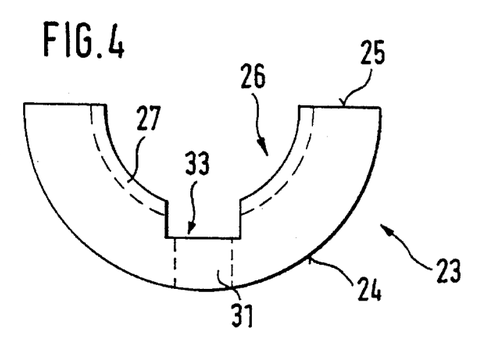
FIG. 4 is a front or back view of tile swivel-bearing element according to FIG. 2, enlarged.
Figure 5:
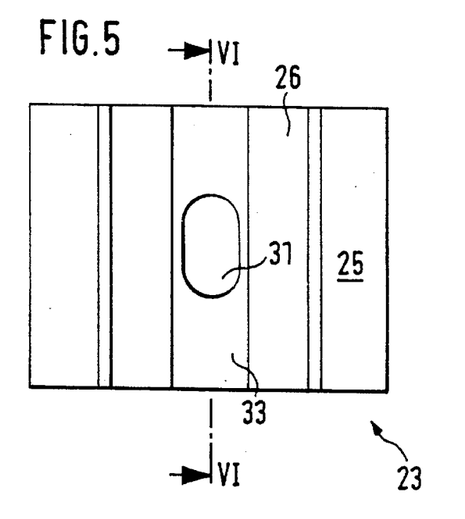
FIG. 5 is a plan view of the swivel-bearing element according to FIG. 2, enlarged.
Figure 6:
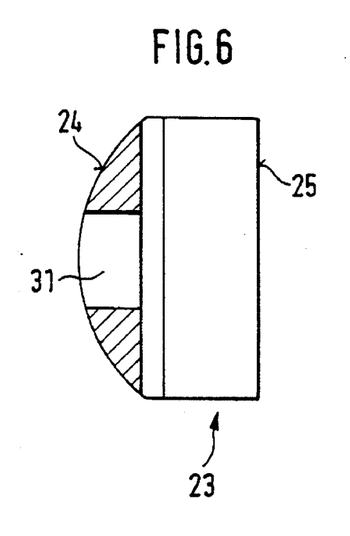
FIG. 6 is a median longitudinal section through the swivel-bearing element according to FIG. 2, enlarged, along the line VI—VI in FIG. 5.

The clamping screw 19 further comprises, as is clearly evident in FIGS. 2 and 3, a pot-like outer edge 21, which encloses the end faces of the two limbs 16, 17 of the tuning-fork-like screw head 15 and holds the latter together in the assembled state.

The floor 22 of the receptacle 18 is approximately concave, according to FIGS. 2 and 8, to correspond to a swivel-bearing element 23 disposed between the floor 22 of the receptacle 18 and the connecting element 14. The bearing surface 24 of the swivel-bearing element 23, which faces the floor 22 of the receptacle 18, has a complementary convex shape.

FIGS. 2 to 6 show a first embodiment of the swivel-bearing element 23. In this embodiment the bearing surface 24, which faces the floor 22 of the receptacle 18, is dish-shaped, in particular hemispherical. In addition, the opposite side 25 of the swivel-bearing element 23, which in the assembled state faces the clamping screw 19, incorporates a groove 26 to receive the rodlike connecting element 14.

The groove 26 to receive the rodlike connecting element 14, which is formed in the swivel-bearing element 23, is approximately semicircular in cross section, corresponding to the cross section of the connecting element 14. Furthermore, machined into the surface of the groove 26 are cross ribs 27, in particular a fine-pitch thread. The cross ribs 27 are an additional means of counteracting axial displacement of the connecting element 14 after the latter has been mounted in the approximately U-shaped receptacle 18 of the retaining means 12, i.e. displacement along the plane that passes through the receptacle 18.

The inner surface 20 of the clamping screw 19, which acts on the rodlike connecting element 14, is convex or conical. Preferably the angle $\phi$ of the conical surface (cf. FIG. 3) amounts to about 5° to 35°, in particular ca. 20°. In the case in which the inner surface 20 of the clamping screw 19 has a conical shape, the tip of the cone is preferably rounded.

The swivel-bearing element 23 is held on the floor 22 of the receptacle 18 in such a way that it can be swiveled both in a plane parallel to the plane passing through the receptacle 18 and also perpendicular to the latter plane. For this purpose, the swivel-bearing element 23 has a semi-dish-shaped, in particular hemispherical bearing surface 24, corresponding to the spherical shape of the floor 22 of the receptacle 18.

Figure 7A:
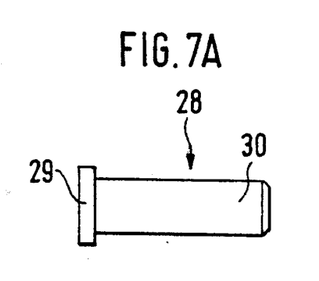
FIG. 7A and 7B are a side view and a plan view of a retaining pin for the swivel-bearing element according to FIG. 2, enlarged.
Figure 7B:
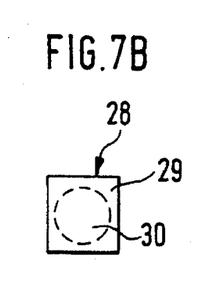

Fixation of the swivel-bearing element 23 at the floor 22 of the receptacle 18 is brought about by a retaining pin 28 like that shown in FIG. 7A and 7B, with a proximally disposed head 29 and a distal end 30. The retaining pin 28, by way of its distal end 30, extends with slight play through a slot 31 in the swivel-bearing element 23 that runs parallel to the groove 26 for the rodlike connecting element 14, and can be pressed into a corresponding receiving bore 32 in the floor 22 of the receptacle 18. The head 29 of the retaining pin 28 then comes to rest within a head groove 33 formed in the groove 26 for the rodlike connecting element 14 and oriented in parallel to the previously mentioned slot 31. The head 29 of the retaining pin 28 thus, in the assembled state, is recessed within the associated head groove 33, so that when the swivel-bearing element 23 rotates in a plane parallel to the plane of the slot 31 formed in the swivel-bearing element 23 there is no collision between the head 29 and the rodlike connecting element 14.

The retaining pin 28 is held by way of its distal end 30 in the receiving bore 32 in the floor 22 of the receptacle 18 with a force fit, strong sliding fit or the like.

In an alternative form, not illustrated in detail, the swivel-bearing element 23 can also be fixed at the floor 22 of the receptacle 18 by way of a pin projecting beyond its bearing surface 24 which faces the floor 22 of the receptacle 18, this pin being held with slight pressing in a seating groove (not illustrated) in the floor 22 of the receptacle 18, which extends parallel to the plane passing through the receptacle 18. It is likewise conceivable, in a further alternative form, that the swivel-bearing element 23 is fixed at the floor 22 of the receptacle 18 by way of a pin projecting above the latter, which is held with slight pressing in a seating groove formed, in particular as a continuous groove, in the bearing surface 24 of the swivel-bearing element 23, i.e. the surface facing the floor 22 of the receptacle 18, this seating groove being oriented in parallel to the groove 26 for the rodlike connecting element 14.

Figure 9:
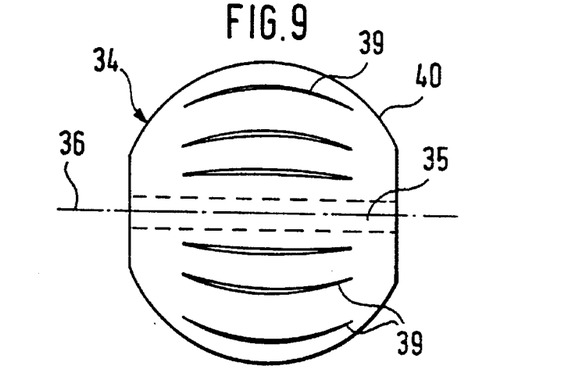
FIG. 9 is a plan view of the swivel-bearing element according to FIG. 8.
Figure 10A:
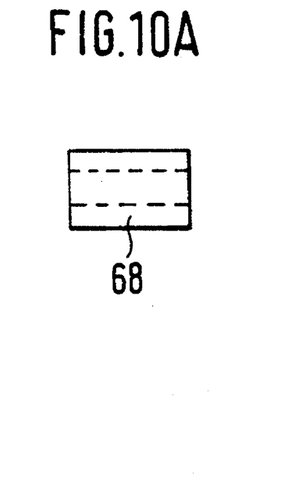
FIG. 10A to 10D are side views of distance rings and distance sleeves provided in accordance with the invention, with various axial widths.
Figure 10B:
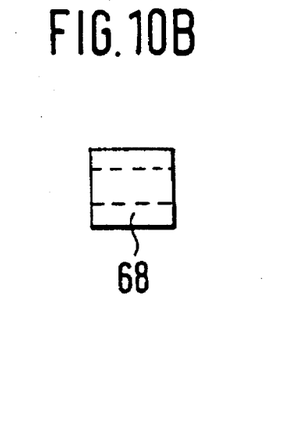
Figure 10C:
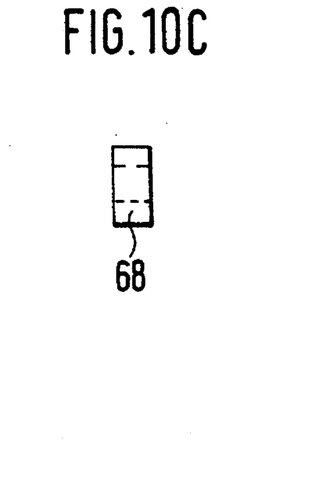
Figure 10D:
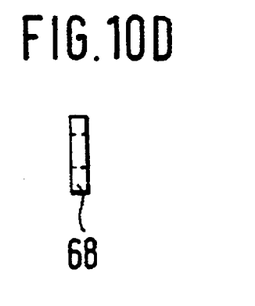

FIGS. 8 and 9 show a second embodiment of the swivel-bearing element 23. In this embodiment the floor 22 of the receptacle 18 has approximately the form of a ball socket. The swivel-bearing element 23 itself is constructed as a spherical sleeve 34 that can be slid along the connecting element 14, which includes a radial gap or slit 35 oriented approximately parallel to the axis of rotation 36 of the spherical sleeve 34 and is provided for radial resilience.

Because the first and second embodiments of the system 10 according to FIG. 2 and FIG. 8, respectively, are largely consistent in other respects, the same components are identified by identical reference numerals.

As is clearly evident in FIG. 8, the connecting element 14 can be received by each retaining means 12 and fixed therein by way of the spherical sleeve 34. The spherical sleeve 34 associated with each retaining means 12 can be simply, rapidly and effortlessly slid along the connecting element 14 because of the approximately circular cross section of the latter.

The spherical sleeve 34 together with the connecting element 14 can be set into the head 15 of the retaining means 12 and be secured and fixed therein by means of the clamping screw 19. The U-shaped receptacle 18 defined by two limbs 16, 17, which receives the spherical sleeve 34 and the connecting element 14, coincides substantially with the plane passing through the connecting element 14 or the median longitudinal plane of the retaining means 12, which in FIG. 2 extends perpendicular to the plane of the page. The spherical sleeve 34 is seated largely without play in the one or more retaining means 12.

In correspondence with FIG. 1, the retaining means 12 is so constructed that the swivel-bearing element 23—i.e., the spherical sleeve 34—together with the connecting element 14 can be swiveled after having been secured in the retaining means 12 by means of the clamping screw 19. The amount of rotation possible for the swivel-bearing element 23 and connecting element 14 within the receptacle of the retaining means 12 depends on the distance between and height of the two limbs 16, 17 of the tuning-fork-like head 15. Accordingly, the swivel-bearing element 23 and the connecting element 14 can be swiveled in the median longitudinal plane of the retaining means 12 over an angle $\alpha$ of 15° to 45°, preferably 30°, and in the plane of the retaining means 12 transverse or perpendicular to the median longitudinal plane of the retaining means 12, i.e. perpendicular to the plane of the page, over an angle β of 1° to 20°, preferably 3°, with respect to the retaining means 12.

According to FIG. 8 the spherical sleeve 34 can be brought into contact with the floor 22 of the receptacle 18 of the retaining means 12 by way of its bearing surface 24. The floor 22 is substantially spherically concave and adapted to the form of the spherical sleeve 34. Thus the spherical sleeve 34 is in contact with the floor 22 of the receptacle 18 of the retaining means 12 over a large surface. In particular, the floor 22, against which the spherical sleeve 34 comes to rest, has the basic form of an inward-tapering cone as shown in FIG. 8. As a result, an additional radial clamping action is exerted on the spherical sleeve when it is pressed against the floor 22 by the clamping screw 19, and this force is ultimately transferred to the rodlike connecting element 14 so that it is held more securely.

The spherical sleeve 34 shown in FIG. 8 includes, as previously mentioned, a radially oriented gap or slit 35, extending approximately in the direction of the axis of rotation 36 of the spherical sleeve 34, which provides radial resilience. Substantially diametrically opposed to the gap or slit 35 is another groove 38 in the inner wall 37 of the spherical sleeve 34. This groove increases the spring action of the spherical sleeve 34 when it is fixed in the receptacle 18 of the retaining means 12 by the clamping screw 19. Accordingly, the clamping action between the spherical sleeve 34 and the connecting element 14 is also enhanced. This arrangement reliably eliminates the possibility that the connecting element 14 will detach itself or shift axially after the system has been implanted.

According to FIG. 9, the spherical sleeve 34 is provided with several notches 39, formed in the outer surface 40 and arranged about in parallel to the axis of rotation 36 of the spherical sleeve 34. The notches 39 allow the spherical sleeve 34, after it has been set into the receptacle 18 of the retaining means 12, to be rotated about its axis of rotation 36 by means of a raspatory, spatula or similar instrument. In this way the gap or slit 35, as shown in FIG. 8, can simply be brought into a lateral position, in which the greatest possible resilience and hence clamping can be achieved.

According to FIG. 8, the spherical sleeve 34 abuts against the inner end face 41 of the clamping screw 19. This surface 41 may be flat or even, or it may be rounded or in particular have the form of an annulus. In the last case the surface 41 is preferably matched to the shape of the spherical sleeve 34.

The clamping screw 19 can be screwed into the receptacle 18 of the retaining means 12. For this purpose the clamping screw 19 comprises a projection 42 with an external screw thread 43. The external thread 43 cooperates with an internal thread 44 on the inner surfaces of the two limbs 16, 17 of the receptacle 18. The inner end face 41 of the clamping screw 19, which abuts against the spherical sleeve 34, in this embodiment is provided on the inner surface 46 of the projection 42.

Figures 12, 13, 14:
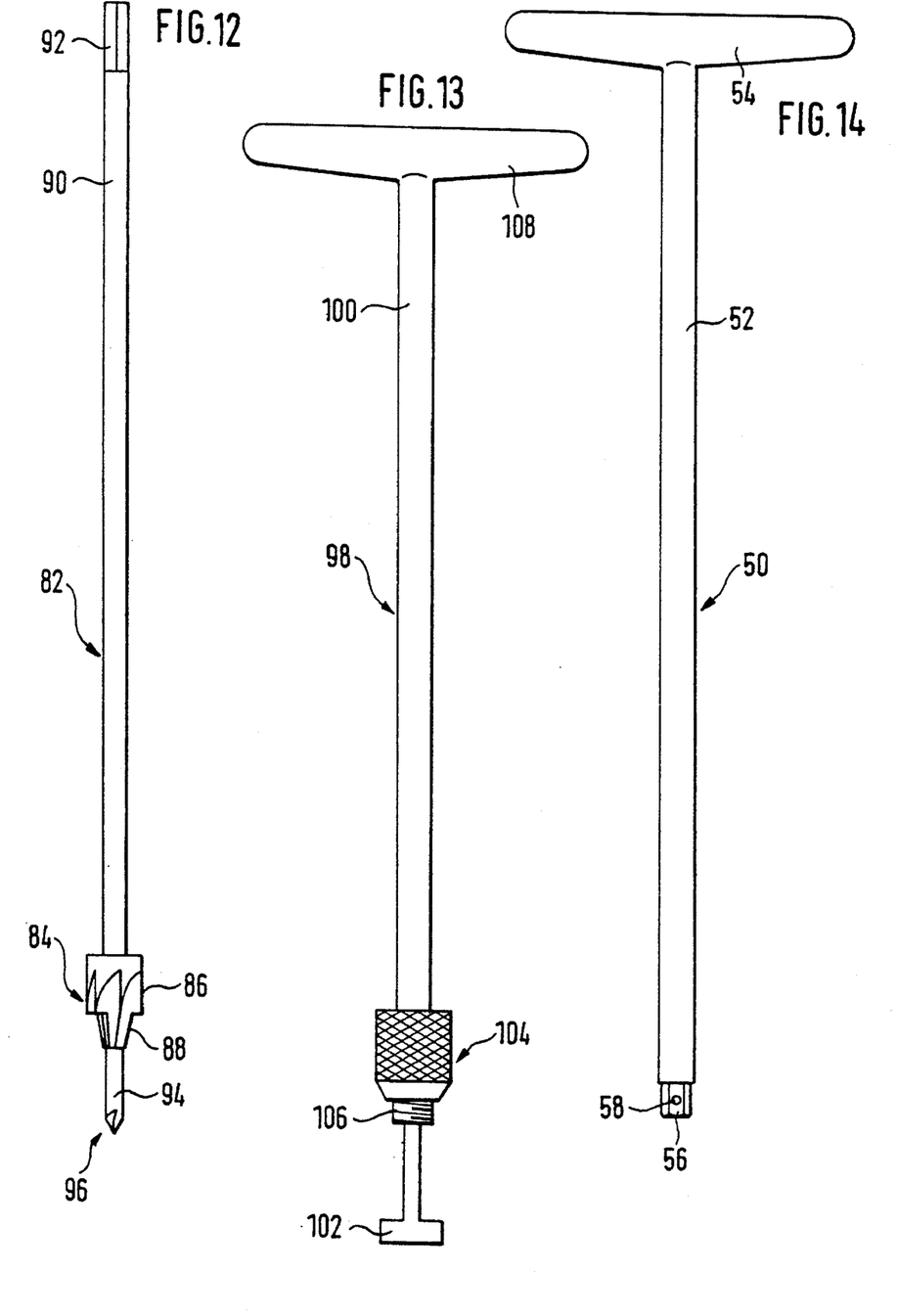
FIG. 12 is a side view of an embodiment of a routing instrument constructed in accordance with the invention.
FIG. 13 is a side view of an embodiment of a first screw instrument constructed in accordance with the invention.
FIG. 14 is a side view of an embodiment of a second screw instrument constructed in accordance with the invention.

So that the clamping screw 19 can be reliably screwed in and out, here it is provided with a hexagon socket 48 for a screw instrument 50 corresponding to FIG. 14.

The screw instrument 50 illustrated in FIG. 14, which serves to tighten the clamping screw 19 at the head 15 of the retaining means 12, comprises a shaft 52 and a handle 54 attached to one end thereof. At the other end of the shaft 52 is a hexagon insert bit 56 corresponding to the hexagon socket 48 of the clamping screw 19. In addition, at one surface of the hexagon insert bit 56 there is provided a ball 58 that can be depressed approximately perpendicularly to the effective surface, against the action of a spring, and that corresponds to a complementary recess in the effective surfaces of the hexagon socket 48.

As shown in FIGS. 1, 2 and 8, the retaining means 12 is constructed as a pedicle screw with a section 60 having a self-tapping screw thread 62. The thread 62 includes a longitudinal slot in the region 64 of its first turns, to remove the bone material of the vertebra.

Between the head 15 of the pedicle screw and the screw thread 62 there is a section 66 that tapers toward the tip of the screw and has the form of a truncated cone. The section 66 serves to provide close-fitting contact with a correspondingly shaped, previously routed-out excavation in the bone material of the vertebra, so as to support the usually very strong shear forces that are produced. In addition, distance rings 68 of varying axial width, examples of which are illustrated in FIG. 10A to 10D, can be set onto the truncated-cone-shaped section 66.

Figure 11:
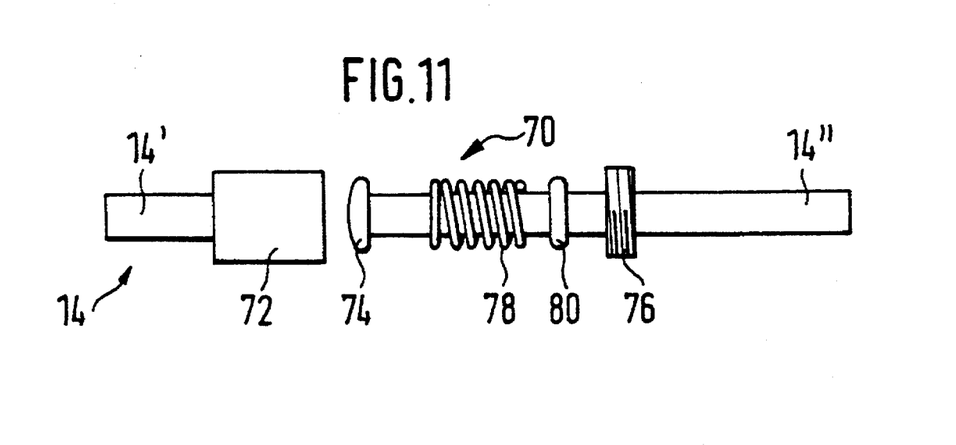
FIG. 11 is an exploded drawing of a connecting element with a universal joint.

As shown in FIG. 11, the connecting element 14 in the form of a bending-resistant rod is additionally provided with a universal joint 70, disposed between two retaining means 12 (not shown in FIG. 5 [sic]). The universal joint 70 connects two parts 14', 14" of the connecting element 14.

The universal joint 70 according to FIG. 11 comprises an approximately axially oriented pot-shaped receiving element 72, which is rigidly connected to the one part 14' of the connecting element 14. The universal joint 70 also comprises a thickening 74 disposed at the end of the other part 14" of the connecting element 14. This is received by the pot-shaped receiving element 72. In the present case the thickening 74 has the form of a rounded disk, i.e. it is flange-like. The thickening 74 with the other part 14" of the connecting element 14 is held in the pot-shaped receiving element 72 of the one part 14' of the connecting element 14 by way of a threaded ring 76.

The universal joint 70 is further formed in such a way that the two parts 14', 14" of the connecting element 14 can carry out not only a sideways rotational movement so that an angle is formed between them, but also a translational movement in the axial direction. Such a translational movement in the axial direction is preferably made under the influence of spring forces. Accordingly, in the receiving element 72 of the universal joint 70 there is disposed a (pressure) coil spring 78, which is inserted between the thickening 74 of the other part 14" of the connecting element 14 and the threaded ring 76 attached to the receiving element 72 of the one part 14' of the connecting element 14 with its underlying shim 70 [sic]. By selecting the length of the pot-shaped receiving element 72 and suitably dimensioning the coil spring 78, it is possible to vary the translational movement of the two parts 14' 14" of the connecting element 14 as desired, so as to adapt it to the particular application.

For the implantation and/or removal of the system 10 for osteosynthesis at the vertebral column, in particular for the stabilization of spinal segments, still another tool is provided, namely a routing instrument 82 to form an excavation in the bone material of the spinal segment. The routing instrument 82, as shown in FIG. 12, comprises a router head 84 with a total of two cutting surfaces 86, 88. The one cutting surface 88 is provided to produce an excavation in the shape of a truncated cone, which tapers inward within the bone material of the vertebra so as to correspond to the shape of the section 66 of the retaining means 12. The other cutting surface 86, in contrast, serves to produce a cylindrical excavation in the bone material of the spinal segment, corresponding to the shape of the head 15 of the retaining means 12. The router head 84 is attached to the distal end of a shaft 90. At the proximal end of the router head 84 [sic] a profile is formed that can be inserted into a corresponding machine-driven chuck for power-operated rotation of the router head 84. The routing instrument 82 further comprises a centering spike 94 with a cutting surface 96 for advance drilling.

Finally, yet another screw instrument 98 is provided according to FIG. 13. This serves to screw the retaining means 12 into the bone material of the spinal segment. It in turn consists of a shaft 100, at the distal end of which the retaining means 12 can be detachably attached (not shown), such that the median longitudinal axes of retaining means 12 and shaft 100 coincide. According to FIG. 13, the screw instrument 98 also bears at its distal end a cross bar 102, the cross section of which corresponds to that of the connecting element 14. Thus the cross bar 102 can be placed in the seating groove 26 of the swivel-bearing element 23 according to FIG. 4, in order to bring the corresponding torque to bear on the two limbs of the pedicle-screw head 15. In this position the cross bar is held by way of a threaded sleeve 104. The latter is displaceably mounted on the shaft 100 and is provided with an external screw thread 106, which cooperates with the internal thread 44 in the head 15 or the receptacle 18 of the retaining means 12 (pedicle screw). The threaded sleeve also comprises a knurled section to facilitate screwing in and out. There is a spindle-shaped handle 108 at the proximal end of the shaft 100.

All the characteristics disclosed in the application documents are claimed as essential to the invention, to the extent that they are new to the state of the art singly or in combination.

I claim:

1. A securement unit for attaching at least one elongated connecting element (14) to a portion of a spinal segment for osteosynthesis of the vertebral column and stabilizing a spinal segment comprising, a connecting member including a retaining element (12) for attachment to a vertebra and a U-shaped head (15) having spaced limbs (16, 17) forming a substantially U-shaped receptacle (18) adapted to receive the connecting element (14), said limbs being threaded, a clamping screw (19) having a threaded portion adapted to be screwed into the threaded receptacle (18), said receptacle (18) having an inner end floor (22) with a concave shape, a swivel-bearing element (23) disposed in engagement with said floor (22), said element (23) having a bearing surface (24) facing the floor (22) of the receptacle (18), said bearing surface having a convex shape, said concave shape of said floor and said convex shape of said swivel-bearing element surface having complementing bearing surfaces, said bearing surface (24) of the swivel-bearing element (23), being substantially hemispherical, said swivel-bearing element having an outer side exposed to said clamping screw (19) with said clamping screw threaded into said receptacle, said outer side having a groove (26) adapted to receive the elongated connecting element (14), said head further comprising a retaining member firmly and swivelely securing said swivel-bearing element to said floor.

2. The securement unit of claim 1 further including said connecting element, and wherein said groove (26) is substantially semicircular in cross section, said connecting element (14) having a similar corresponding cross section to said cross section of the groove.

3. The securement unit of claim 2,
wherein said groove (26) includes machined cross ribs (27).

4. The securement unit of claim 1, wherein said clamping screw (19) has an inner end face with a conical shape and a rounded end.

5. The securement unit of claim 1, wherein said swivel-bearing element (23) swivels on said hemispherical shape bearing surface both in a plane parallel to a plane passing through the receptacle (18) and also in a plane perpendicular to the receptacle.

6. The securement unit of claim 5, wherein said retaining member is a round pin projecting beyond said bearing surface (24) facing the floor (22) of the receptacle (18), said floor (22) having a securement bore receiving said pin, said pin being secured with a pressure fit in said bore.

7. The securement unit of claim 5, wherein said support includes a pin projecting above the floor, said floor having a securement bore, said pin being secured with a pressure fit in said securement bore, said bearing element having a seating groove (33) being a continuous groove formed in the groove (26) of the swivel-bearing element (23), said seating groove (33) extending in parallel to the groove (26) that receives the elongated connecting element (14).

8. The securement unit of claim 5,
said floor includes a bore (32), said groove (26) having a head groove (33) and having a slot (31) aligned with said bore, said slot and said head groove extending parallel to the connecting element receiving groove (26), said retaining member being a retaining pin having a proximally disposed head (29) and a distal end (30), the swivel-bearing element (23) being fixed to the floor (22) of the receptacle (18) by said retaining pin (28), the distal end (30) of said pin adapted to be inserted with slight play through said slot (31) and into said bore (32) in the floor (22) of the receptacle (18) with said head (29) abutting said head groove (33).

9. The securement unit of claim 8, wherein said head of the pin (29) is located within the associated head groove (33) and below the connecting element receiving groove of said swivel-bearing element (23).

10. The securement unit of claim 8, wherein said retaining pin (28) and bore are connected by a forced pressure fit.

11. The securement unit of claim 1, characterized in that said retaining element (12) has the form of a pedicle screw with a thread (62) having a proximal end near the head and a distal end.

12. The securement unit of claim 11, wherein said thread includes a plurality of turns extending from said head, and including a longitudinally extended slit near the distal end of the screw to allow removal of the bone material.

13. The securement unit of claim 11,
wherein the pedicle screw comprises a head (15) and a spaced threaded section including said thread (62) connected by a connecting section (66) that tapers from the head toward the threaded section and with taper bearings in the shape of a truncated cone, said pedicle screw adapted to provide a close-fitting contact within a corresponding performed excavation in the bone of the spinal segment.

14. The securement unit of claim 13,
including distance rings (68) varying in axial width and adapted to be set onto the truncated-cone section (66) of the pedicle screw.

15. The securement unit of claim 1,
wherein the retaining element (12) has the form of a hook adapted for anchoring at a pedicle and below an articular process and at a transverse process.

16. The securement unit of claim 1, further including said connecting element (14), wherein said connecting element is an elongated rod having a significant resistance to bending.

17. The securement unit of claim 16, wherein the connecting element (14) is a bending-resistant rod including at least one joint (70) disposed between said two retaining elements (12).

18. The securement unit of claim 1, further including said elongated connecting element and wherein the elongated connecting element (14) is a bendable wire.

19. The securement unit of claim 1, wherein at least one of said swivel-bearing element (23) and said retaining element (12) and said clamping screw (19) and said connecting element (14) is made of a non-rusting material including titanium and a titanium alloy.

* * * * *